(12) United States Patent
Sasaki et al.

(10) Patent No.: US 7,520,155 B2
(45) Date of Patent: Apr. 21, 2009

(54) GAS DETECTION APPARATUS AND METHOD

(75) Inventors: Takashi Sasaki, Saitama (JP); Hidetoshi Oishi, Saitama (JP); Takashi Saito, Saitama (JP); Akihiro Suzuki, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 338 days.

(21) Appl. No.: 11/285,957

(22) Filed: Nov. 22, 2005

(65) Prior Publication Data

US 2006/0113199 A1 Jun. 1, 2006

(30) Foreign Application Priority Data

Nov. 26, 2004 (JP) ............................. 2004-343008

(51) Int. Cl.
*G01N 27/00* (2006.01)
(52) U.S. Cl. ....................................................... 73/1.06
(58) Field of Classification Search .................. 73/1.06, 73/23.2
See application file for complete search history.

(56) References Cited

U.S. PATENT DOCUMENTS

| | | | |
|---|---|---|---|
| 6,200,443 B1 * | 3/2001 | Shen et al. | 204/401 |
| 6,409,969 B1 * | 6/2002 | Streicher et al. | 422/94 |
| 6,568,240 B1 * | 5/2003 | Sato et al. | 73/1.07 |
| 6,611,208 B1 * | 8/2003 | Ketler | 340/632 |
| 6,896,781 B1 * | 5/2005 | Shen et al. | 204/415 |
| 2006/0042965 A1 * | 3/2006 | Sasaki et al. | 205/784 |

FOREIGN PATENT DOCUMENTS

| | | |
|---|---|---|
| JP | 62-64938 | 3/1987 |
| JP | 06-223850 | 8/1994 |
| JP | 2000-146885 | 5/2000 |
| JP | 2003-294675 | 10/2003 |
| JP | 2005-091324 | 4/2005 |
| JP | 3746778 | 4/2005 |

\* cited by examiner

*Primary Examiner*—Hezron Williams
*Assistant Examiner*—Rodney T Frank
(74) *Attorney, Agent, or Firm*—Fish & Richardson P.C.

(57) ABSTRACT

A gas detection chamber in which a gas sensing element is provided to detect a component of a gas allowed into the gas detection chamber is heated by a heater, and an output of the heater is regulated by a heater regulator. The heater regulator is adapted to cause the heater to continue to heat the gas detection chamber (preferably but not necessarily, the output of the heater is caused to lower) when an anomaly detection device detects an anomaly of the gas sensing element.

12 Claims, 4 Drawing Sheets

GAS DETECTION APPARATUS AND METHOD

BACKGROUND OF THE INVENTION

Apparatuses and methods consistent with the present invention relate to detection of a gas. Particularly, the present invention relates to an apparatus and a method for detecting a gas in humid surroundings.

Gas sensors for detecting a fuel gas (hydrogen gas) contained in an exhaust gas of a polymer electrolyte fuel cell are known in the art. For example, a gas sensor disclosed in JP 6-223850 A (see paragraphs 0013 and 0014; FIG. 1) is provided in an exhaust system for discharging a cathode exhaust gas (air) of the fuel cell. This gas sensor is adapted to detect a fuel gas that could accidentally leak from an anode (fuel pole) to a cathode (oxidant pole) through a polymer electrolyte membrane, and used to prevent the fuel gas from being released into the atmosphere.

In general, the exhaust gas of a fuel cell contains a high concentration of water in the form of water vapors or drops derived from water used to humidify the polymer electrolyte membrane or water generated by an electrochemical reaction of the fuel gas (hydrogen gas) and the air (oxygen). On occasion, the water that has condensed from the steam and has thus been contained in the exhaust gas would adhere to a gas sensing element of the gas sensor, which could result in anomalies in performances of the sensing element such as sensitivity for detecting the fuel gas.

With this in view, a gas sensor with a built-in heater has been proposed, for example as disclosed in JP 2003-294675 A (see paragraph 0012; FIG. 4), which can prevent adhesion of the condensed water to the gas sensing element. This gas sensor heats the exhaust gas using the built-in heater to lower the relative humidity.

Typically, when an anomaly occurs in the gas sensor with a built-in heater, the output of the heater is suspended. However, if the heater is suspended without exception when any anomaly appears, including those determined temporarily as an anomaly for example as a result of adhesion of water drops in the exhaust gas to the gas sensing element, such suspension of the heater would cause water condensed more from vapors in the exhaust gas to be further adhered to the gas sensing element. Thus, increase in the amount of water adhered to the gas sensing element would disadvantageously result in prolonged downtime of the gas sensor.

Accordingly, it would be desirable to provide a gas detection apparatus and a gas detection method in which a gas sensor can be swiftly returned to a normal operable state from an abnormal state (with anomalies) caused by adhesion of water to its gas sensing element.

Illustrative, non-limiting embodiments of the present invention overcome the above disadvantages and other disadvantages not described above. Also, the present invention is not required to overcome the disadvantages described above, and an illustrative, non-limiting embodiment of the present invention may not overcome any of the problems described above.

SUMMARY OF THE INVENTION

It is an aspect of the present invention to provide a gas detection apparatus which comprises a gas detection chamber, a gas sensing element, an anomaly detection device, a heater, and a heater regulator. The gas detection chamber is adapted to receive a gas. The gas sensing element is provided in the gas detection chamber to detect a component of the gas. The anomaly detection device is provided to detect an anomaly of the gas sensing element. The heater is provided to heat the gas detection chamber. The heater regulator is provided to regulate an output of the heater. The heater regulator is adapted to cause the heater to continue to heat the gas detection chamber when the anomaly detection device detects the anomaly of the gas sensing element.

Typically, the gas detection apparatus in one embodiment of the present invention is used to detect a component of a gas having a high relative humidity, and the heater is adapted to lower a relative humidity of the gas so that condensed water derived from vapors in the gas detection chamber can be reduced and prevented from adhering to the gas detecting element. The anomaly of the gas sensing element may preferably but not necessarily be detected by measuring an electric current using an electric current meter (ammeter) or an electric resistance using an electric resistance meter in the gas sensing element. In this instance, the anomaly of the gas sensing element could be detected as a result of adhesion of water to the gas sensing element. Since the heater regulator of the above gas detection apparatus is adapted to cause the heater to continue to heat the gas detection chamber when the anomaly detection device detects the anomaly of the gas sensing element, the condensed water that would otherwise be generated in the gas detection chamber can be reduced by the continuously operating heater according to the above gas detection apparatus in comparison with a conventional gas detection apparatus in which a heater is caused to stop upon detection of such an anomaly. Consequently, the above gas detection apparatus is advantageous in that adhesion of water to the gas sensing element is not increased.

In the above gas detection apparatus, preferably but not necessarily, the heater regulator may be configured to cause the output of the heater to lower when the anomaly detection device detects the anomaly of the gas sensing element. This advantageously serves to prevent overheating of the gas detection chamber by the heater. In this embodiment, the heater regulator may preferably but not necessarily be configured to cause the output of the heater to return to a normal operating level when the anomaly detection device detects absence of the previously detected anomaly of the gas sensing element.

The above gas sensing element may preferably but not necessarily be selected from the group consisting of a catalytic combustible sensing element, a semiconductor sensing element, a solid-electrolyte sensing element, an electrochemical sensing element, a field-effect transistor sensing element, a diode sensing element, and an adsorption effect transistor sensing element.

The component of the gas to be detected by the gas sensing element may preferably but not necessarily include any one of combustible hydrocarbon, nitrogen oxide, sulfur oxide, hydrogen sulfide, carbon monoxide, carbon dioxide, halogen, halogenated hydrogen, and ammonia.

In another aspect of the present invention, there is provided a gas detection method which comprises: allowing a heater to heat a gas detection chamber in which a gas sensing element is provided, while allowing a heater regulator to regulate an output of the heater; allowing the gas sensing element to sense a component of the gas in the gas detection chamber heated by the heater; allowing an anomaly detection device to detect an anomaly of the gas sensing element; and allowing the heater regulator to cause the heater to continue to heat the gas detection chamber when the anomaly detection device detects the anomaly of the gas sensing element. This method may exert the same advantageous effects as described above in connection with the gas detection apparatus.

In the above method, the allowing the heater regulator to cause the heater to continue to heat the gas detection chamber may comprise allowing the heater regulator to cause the output of the heater to lower. Optionally, the allowing the heater regulator to cause the heater to continue to heat the gas detection chamber may further comprise allowing the heater regulator to cause the output of the heater to return to a normal operating level when the anomaly detection device detects absence of the previously detected anomaly of the gas sensing element.

A fuel cell system provided as yet another aspect of the present invention comprises: a fuel cell stack comprised of a plurality of stacked fuel cells each having an anode and a cathode, to generate electricity by electrochemical reaction occurring at a high humidity between a hydrogen fuel gas supplied to the anode and an oxygen gas supplied to the cathode; a diluter provided downstream of the fuel cell stack to dilute an anode exhaust gas discharged from the anode with a cathode exhaust gas discharged from the cathode; and a gas detection apparatus as described above, wherein the component to be detected is hydrogen in the gas passing through the fuel cell system. In one embodiment, the gas detection chamber of the gas detection apparatus may be provided to receive the diluted anode exhaust gas discharged from the diluter.

BRIEF DESCRIPTION OF THE DRAWINGS

The above aspects, other advantages and further features of the present invention will become more apparent by describing in detail illustrative, non-limiting embodiments thereof with reference to the accompanying drawings, in which.

DETAILED DESCRIPTION OF THE EXEMPLARY EMBODIMENT(S)

A detailed description will now be given of a fuel cell system and a gas detection apparatus as one exemplified embodiment of the present invention, and a gas detection method carried out in the fuel cell system.

[Fuel Cell System]

Figure 1:
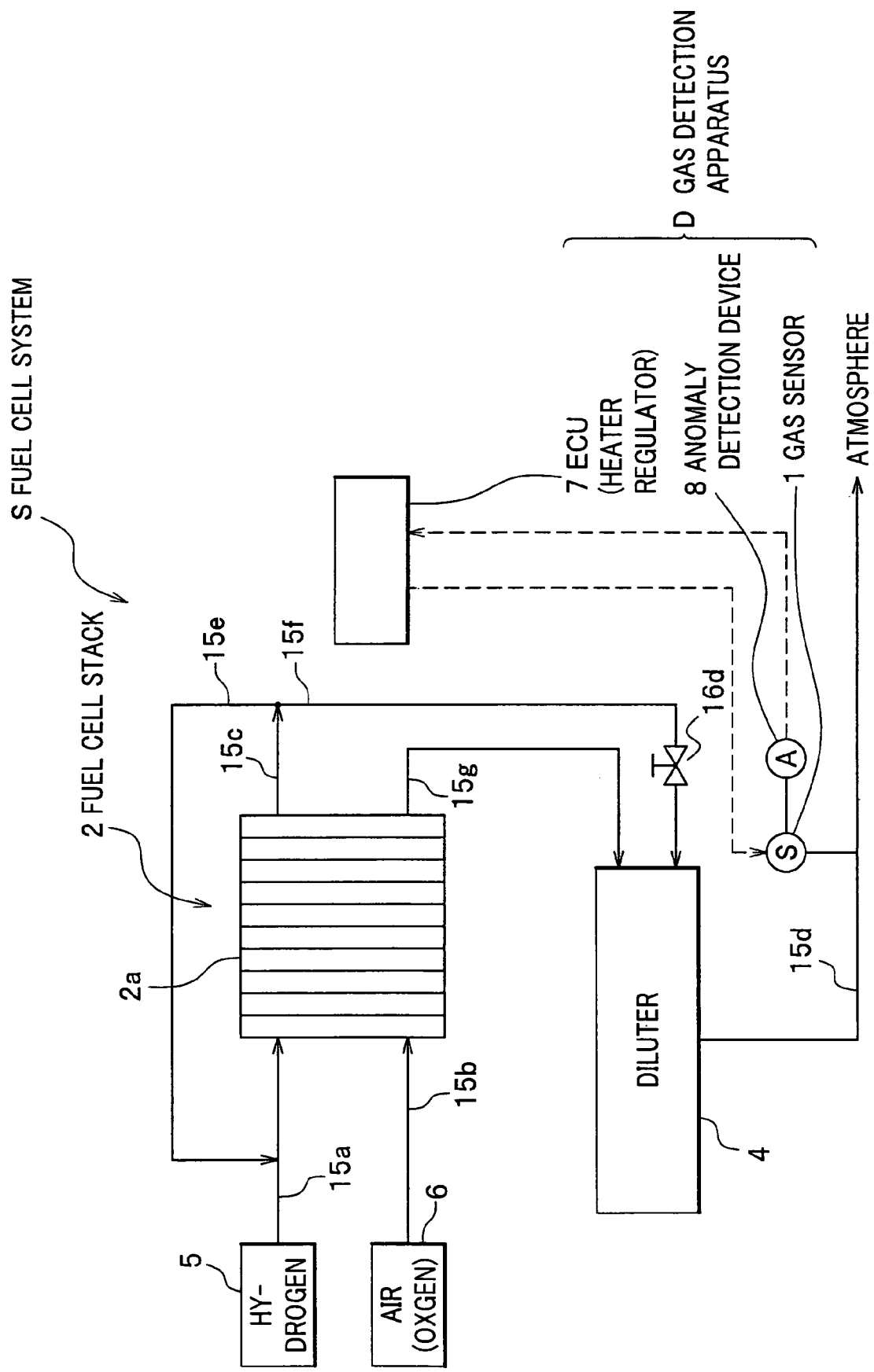
FIG. 1 is a schematic block diagram of a fuel cell system in which a gas detection apparatus according to an exemplary embodiment of the present invention is provided.

Referring now to FIG. 1, a fuel cell system S includes a fuel cell stack 2, a diluter 4 and a gas detection apparatus D. The fuel cell system S further includes a high-pressure hydrogen tank 5 from which is supplied a hydrogen gas for fueling the fuel cell stack 2, a compressor 6 for supplying air as an oxidant to the fuel cell stack 2, a radiator (not shown) for cooling a fuel cell stack 2, and other components.

The fuel cell system 2 is as shown in FIG. 1 comprised of multiple single cells 2a stacked, to generate electricity by electrochemical reaction of the hydrogen gas stored in the high-pressure hydrogen tank 5 and an oxygen gas contained in the air supplied from the compressor 6. An anode side inlet of the fuel cell stack 2 and the high-pressure hydrogen tank 5 are connected by a hydrogen supply line 15a, while a cathode side inlet of the fuel cell stack 2 and the compressor 6 are connected by an air supply line 15b. In other words, the hydrogen gas is supplied to the fuel cell stack 2 through the hydrogen supply line 15a, and the air is supplied to the fuel cell stack 2 through the air supply line 15b. An anode side outlet of the fuel cell stack 2 is connected with a hydrogen exhaust line 15c through which an anode exhaust gas containing a hydrogen gas that has not been consumed in generating electricity is to be discharged.

The hydrogen exhaust line 15c extends from the fuel cell stack 2 to a bifurcation at which a hydrogen circulation line 15e and a purge hydrogen line 15f branch off therefrom. The hydrogen circulation line 15e allows the anode exhaust gas to be flowed back so as to utilize the unconsumed hydrogen gas contained in the anode exhaust gas for generating electricity. The hydrogen circulation line 15e is connected with the hydrogen supply line 15a.

The purge hydrogen line 15f is used to discharge impurities such as a nitrogen gas that would build up in the anode exhaust gas as a result of circulation of the anode exhaust gas (hydrogen gas contained therein) through the hydrogen circulation line 15e. The purge hydrogen line 15f is connected with the diluter 4. A purge valve 16d provided in the purge hydrogen line 15f is adapted to open intermittently, so as to purge the circulated hydrogen gas into the diluter 4. A cathode side outlet of the fuel cell stack 2 is connected with one end of an air discharge line 15g, of which the other end is connected with the diluter 4.

The diluter 4 is provided to dilute the anode exhaust gas (hydrogen gas) discharged through the purge hydrogen line 15f with the cathode exhaust gas (air) discharged through the air discharge line 15g. The diluted anode exhaust gas is discharged into the atmosphere through an exhaust line 15d of which one end is connected with the diluter 4. At this stage, in this fuel cell system S, the gas detection apparatus D is used to detect the concentration of hydrogen gas contained in the gas to be discharged into the atmosphere through the exhaust line 15d, which gas will hereinafter be referred to simply as "exhaust gas". The exhaust gas is the gas subjected to detection in the gas detection apparatus D that will be described below in more detail. The hydrogen gas contained in the exhaust gas includes a hydrogen gas that has been included in the anode exhaust gas as purged, a hydrogen gas that has accidentally leaked from the anode to the cathode through the polymer electrolyte membrane, and so forth. The exhaust gas contains vapors that have been included in the cathode exhaust gas, water drops that are derived from water generated in the process of electric power generation by the fuel cell stack 2, and moisture of other origins which make the exhaust gas humid.

[Gas Detection Apparatus]

Referring to FIG. 1, there is shown a gas detection apparatus D which includes a gas sensor 1, an anomaly detection device 8 for detecting an anomaly of a gas sensing element 12 (see FIG. 2) incorporated in the gas sensor 1, and an electronic control unit (ECU) 7. The ECU 7 serves as a heater regulator provided to regulate an output of a heater 13 that will be described below.

Figure 2:
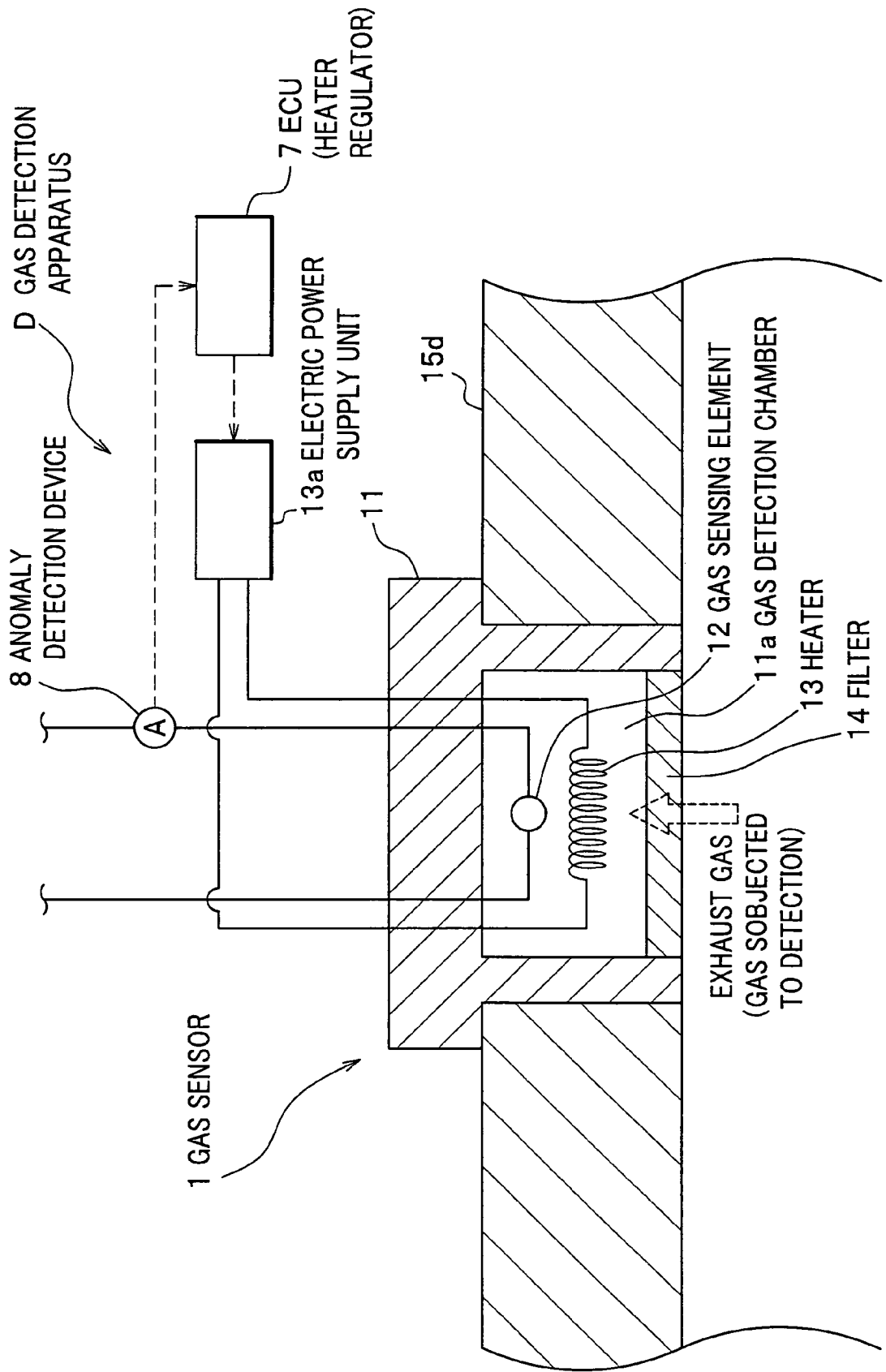
FIG. 2 is an explanatory illustration of a gas detection apparatus according to an exemplary embodiment of the present invention.

The gas sensor 1, as shown in FIG. 2, includes a casing 11, a gas sensing element 12, a heater 13, and a filter 14. Also provided in the gas sensor 1 is a detection circuit (not shown) electrically connected with the gas sensing element 12.

The casing 11 is attached to the exhaust line 15$d$, and a gas detection chamber 11$a$ is formed within the casing 11. The gas detection chamber 11$a$ has an opening with a filter 14, which provides communication with the exhaust line 15$d$. Accordingly, an exhaust gas in the exhaust line 15$d$ is allowed to pass through the filter 14 into the gas detection chamber 11$a$. The filter 14 serves to remove water drops contained in the exhaust gas that is passing therethrough into the gas detection chamber 11$a$.

The gas sensing element 12 is provided in the gas detection chamber 11$a$. Any sensing devices known in the art may be employed for this gas sensing element 12; in this embodiment, exemplarily, a catalytic combustible gas sensor element is used. The catalytic combustible gas sensor element is, as is known in the art, comprised of a coil-shaped platinum wire coated with a catalyst carrier. In this catalytic combustible gas sensor element, the catalyst carrier with which a hydrogen gas has contacted generates heat the amount of which is proportionate to the concentration of the hydrogen gas, and the heat as thus generated causes the temperature of the coil-shaped platinum wire to rise, which in turn raises an electric resistance of the coil-shaped platinum wire. The detection circuit (not shown) electrically connected with the gas sensing element 12 has a structure known in the art, for example, comprised of a Wheatstone bridge configured to measure the electric resistance of the coil-shaped platinum wire. The detection circuit measures the amount of change in electric resistance of the coil-shaped platinum wire which varies with the concentration of the hydrogen gas, and obtains as a gas detection signal a variation of a current passing through or a voltage applied to the coil-shaped platinum wire. The detection circuit outputs the gas detection signal (hereinafter referred to as "hydrogen gas detection signal") to the ECU 7.

The heater 13 is provided to heat the gas detection chamber 11$a$. In this embodiment as illustrated in FIG. 1, the heater 13 is provided in the gas detection chamber 11$a$, though the position of the heater 13 is not limited to this or other specific locations as far as the heater 13 can heat the gas detection chamber 11$a$ efficiently. The heater 13 is adapted to generate heat by conversion of electricity supplied by an electric power supply unit 13$a$. An output of the heater 13 is regulated by the ECU in accordance with a process that will be described later. The electric power supply unit 13$a$ may be of a known structure, for example comprised of a power source, an inverter and other components.

The anomaly detection device 8 is a device to detect an anomaly of the gas sensing element 12, and in the present embodiment is comprised of an ammeter (electric current meter) for measuring an electric current passing through the coil-shaped platinum wire provided in the gas sensing element 12, which electric current will hereinafter be referred to as "current carried in the gas sensing element 12". The ammeter outputs as an anomaly detection signal the current carried in the gas sensing element 12 to the ECU 7.

The ECU 7 may be of a known structure comprised of a central processing unit (CPU) and a semiconductor memory device. The ECU 7 is configured to receive the anomaly detection signal output from the anomaly detection device 8 (ammeter), and to regulate the output of the heater 13 on the basis of the anomaly detection signal, by following the process that will be described later. The ECU is also configured to receive the hydrogen gas detection signal output from the detection circuit connected with the gas sensing element 12, and to determine the concentration of the hydrogen gas contained in the exhaust gas on the basis of the hydrogen gas detection signal.

A description will be given of an operation of the gas detection apparatus D according to an exemplary embodiment of the present invention with reference to the drawings.

Referring to FIG. 1, first, an operation of the fuel cell system S will be described briefly. In the fuel cell system S, as shown in FIG. 1, a hydrogen gas supplied from the high-pressure hydrogen tank 5 passes through a humidifier (not shown) and flows into the fuel cell stack 2, while air supplied from the compressor 6 flows into the fuel cell stack 2. The fuel cell stack 2 then starts to generate electricity using the supplied hydrogen gas and air. An anode exhaust gas discharged from the fuel cell stack 2 through the hydrogen exhaust line 15$c$ contains unreacted hydrogen gas, and thus is flowed through the hydrogen circulation line 15$e$ and the hydrogen supply line 15$a$ back to the fuel cell stack 2 in which the remaining hydrogen gas is utilized, while the purge valve 16$d$ is being closed. Air discharged from the fuel cell stack 2 through the air discharge line 15$g$ is flowed into the diluter 4, and is eventually discharged into the atmosphere.

On the other hand, as impurities have accumulated in the anode exhaust gas (hydrogen gas) circulated for recycled use, the purge valve 16$d$ is opened, so that the anode exhaust gas is allowed to flow through the purge hydrogen line 15$f$ into the diluter 4. As a result, the hydrogen gas contained in the anode exhaust gas is mixed and diluted with the cathode exhaust gas in the diluter 4 to produce an exhaust gas, which is discharged through the exhaust line 15$d$ into the atmosphere. Since the exhaust gas contains vapors and water drops, the gas detection apparatus D has to be able to detect the concentration of hydrogen gas in the exhaust gas that is subjected to detection at high humidities.

Figure 3:
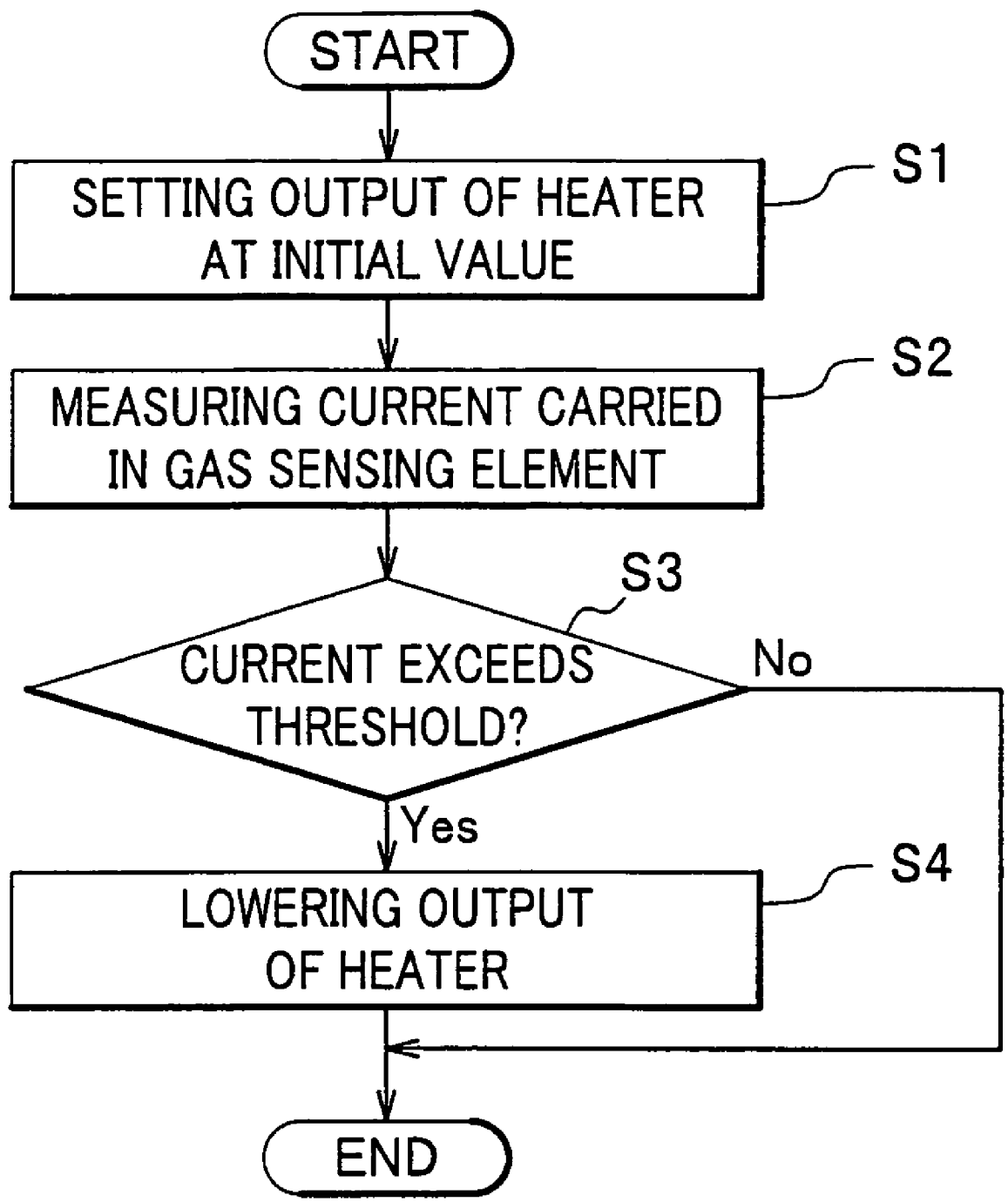
FIG. 3 is a flowchart for explaining an operation of a gas detection apparatus according to an exemplary embodiment of the present invention.
Figure 4A:
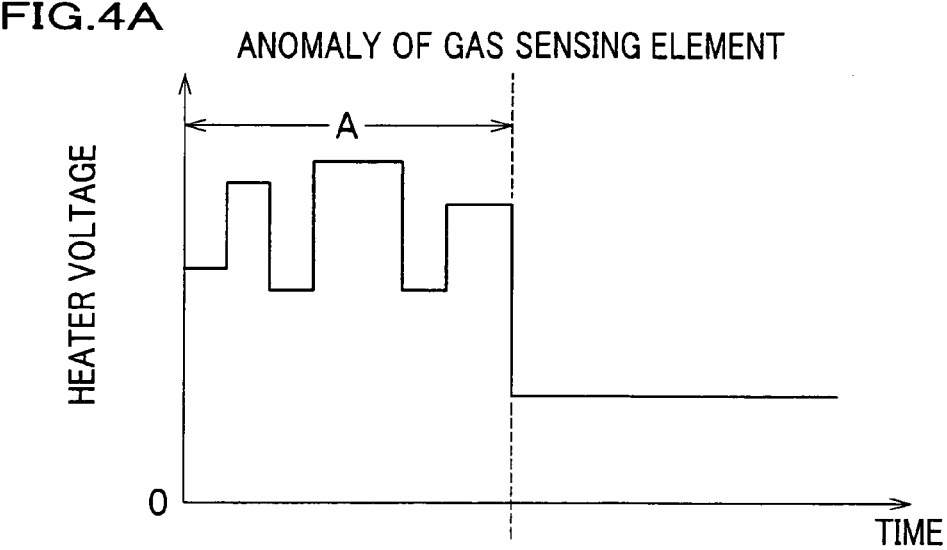
FIG. 4A is a timing chart showing a voltage of a heater provided in a gas detection apparatus according to an exemplary embodiment of the present invention, which varies before and after an anomaly occurs in a gas sensing element of the gas detection apparatus.
Figure 4B:
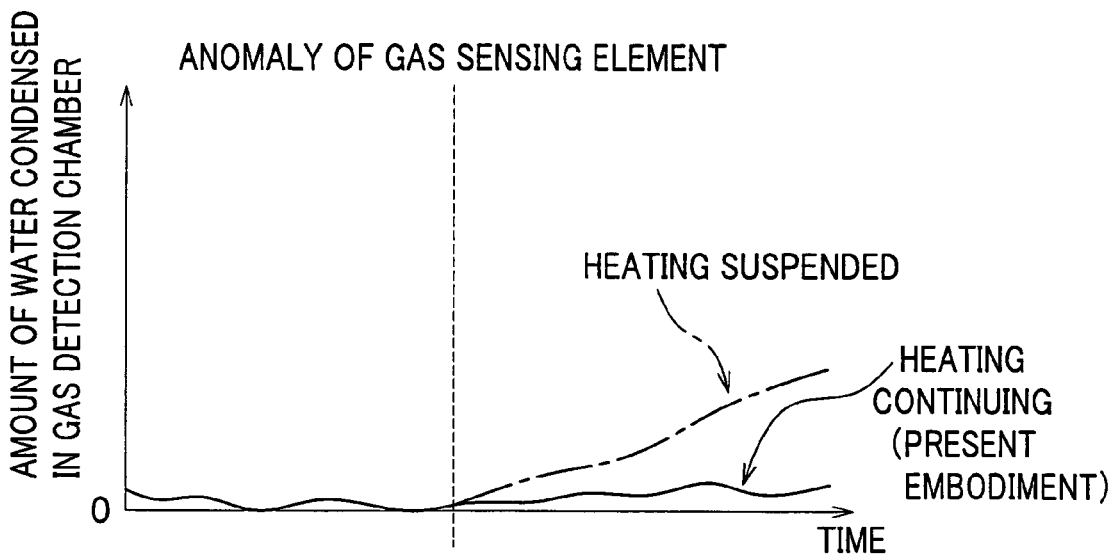
FIG. 4B is a timing chart showing an amount of condensed water in a gas detection chamber of a gas detection apparatus according to an exemplary embodiment of the present invention, which varies before and after an anomaly occurs in a gas sensing element of the gas detection apparatus.

Referring to FIG. 3, when the fuel cell system S (see FIG. 1) starts to operate, the gas detection apparatus D according to the present embodiment regulates the output of the heater 13 at an initial value, so that the heater 13 heats the gas detection chamber 11$a$ (see FIG. 2) to a predetermined temperature and causes the temperature to stay steady (step S1). To be more specific, the ECU 7 instructs the electric power supply unit 13$a$ to set a voltage of the heater 13 at a predetermined value, to thereby regulate the output of the heater 13 at that initial value. This process corresponds to a period of time indicated by A in FIG. 4A. In the present embodiment, the voltage of the heater 13 during this period A is controlled by a duty factor, but may be controlled by a voltage value. Heating of the gas detection chamber 11$a$ by the heater 13 the output of which is regulated as described above reduces a relative humidity in the gas detection chamber 11$a$. Consequently, as shown in FIG. 4B, an amount of water condensed in the gas detection chamber 11$a$ can be kept low during the period corresponding period A of FIG. 4A.

On the other hand, as shown in FIG. 2, the gas sensing element 12 comes in contact with hydrogen gas contained in the exhaust gas flowed through the exhaust line 15$d$ and allowed into the gas detection chamber 11$a$ through the filter 14. Then, change in electric resistance of the coil-shaped platinum wire (not shown) occurs in the gas sensing element 12, and the electric resistance changes in accordance with the concentration of hydrogen gas in the exhaust gas. The detection circuit (not shown) connected with the gas sensing element 12 then outputs to the ECU 7 a hydrogen gas detection signal as described above responsive to the amount of change in the electric resistance of the coil-shaped platinum wire. The ECU that has received the hydrogen gas detection signal in turn determines the concentration of hydrogen gas in the exhaust gas on the basis of the hydrogen gas detection signal. In this manner, the gas sensing element 12 senses the hydrogen gas in the exhaust gas to thereby detect the presence of an impermissible amount of hydrogen in the exhaust gas. When the gas sensing element 12 senses the hydrogen gas contained in the exhaust gas in the gas detection chamber 11a, the possibility for adhesion of water to the gas sensing element 12 is prevented because the relative humidity in the gas detection chamber 11a is reduced by the heater 13.

The anomaly detection device 8 (ammeter) in an exemplary embodiment as shown in FIG. 2 measures an electric current carried in the gas sensing element 12 to thereby detect the presence or absence of an anomaly of the gas sensing element 12 (see step S2 in FIG. 3).

Figure 4C:
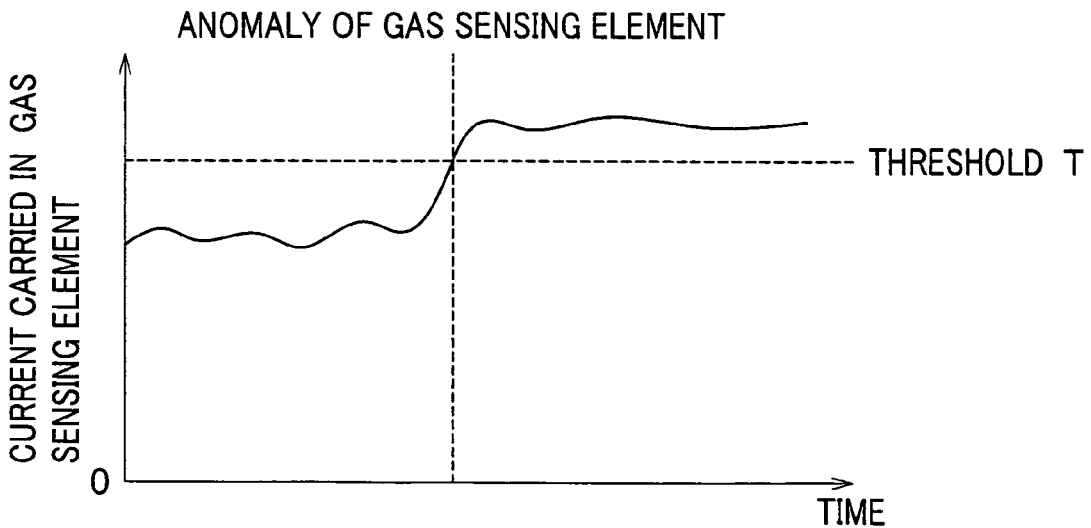
FIG. 4C is a timing chart showing a current carried in a gas sensor or gas sensing element of a gas detection apparatus, which varies before and after an anomaly occurs in the gas sensing element.

The ECU 7 determines whether the electric current carried in the gas sensing element 12 has exceeded a predetermined threshold T (step S3). The threshold T may be defined as a specific value in electric current which is deemed to be abnormal and may be carried in the gas sensing element 12 when electric resistance has lowered in the gas sensing element 12 for some reason, presumably as a result of adhesion of condensed water or the like to the gas sensing element 12. In this embodiment, this specific value to be used as threshold T of electric current carried in the gas sensing element 12 is stored in a semiconductor memory provided in the ECU 7. When the measured electric current in the gas sensing element 12 has exceeded the threshold T as shown in FIG. 4C, the ECU 7 determines that an anomaly has occurred in the gas sensing element 12.

As shown in FIG. 3, if the electric current carried in the gas sensing element 12 as measured in the anomaly detection device 8 (ammeter) exceeds the threshold T (YES in step S3), the gas detection apparatus D lowers the output of the heater 13 (step S4). To be more specific, the ECU 7 instructs the electric power supply unit 13a (see FIG. 2) to set a voltage of the heater 13 such that the output of the heater 13 is caused to lower. Consequently, as shown in FIG. 4A, even after occurrence of anomaly in the gas sensing element 13, a voltage continues to be applied to the heater 13 so that the heater continues to heat the gas detection chamber 1a, though the voltage after the occurrence of anomaly is lower than that which was applied before that (during the period A). In an exemplary embodiment as illustrated in FIG. 4A, the output of the heater 13 as lowered in step S4 is approximately 25% of the output of the heater 13 as set at an initial value in step S1. The voltage of the heater 13 as lowered in step S4 may be controlled either by a duty factor or by a voltage value.

Since heating of the gas detection chamber 11a continues as described above in the present embodiment, the relative humidity of the exhaust gas in the gas detection chamber 11a is caused to lower. Resultantly, as shown in FIG. 4B, the gas detection apparatus D that allows the heater 13 to continuously heat the gas detection chamber 11a even after an anomaly is detected in the gas sensing element 12 causes the amount of water condensed in the gas detection chamber 11a to be reduced further in comparison with a conventional apparatus that allows a heater to stop its heating operation, of which the amount of water condensed in the gas detection chamber 11a is indicated by alternate long and short dash lines. In other words, in the gas detection apparatus D according to the present embodiment, adhesion of water to the gas sensing element 12 is not facilitated or increased even after the detection of anomaly in the gas sensing element 12. The water adhered to the gas sensing element 12 will be removed by heat applied by the heater 13, and then the gas sensor 1 is returned to a normal operable state.

On the other hand, if the ECU 7 determines that no anomaly has been detected in the gas sensing element 12 (NO in step S3), the output of the heater 13 is maintained at the initial value and the gas detection chamber 11a continues to be heated. Accordingly, the low relative humidity of the exhaust gas in the gas detection chamber 11a is maintained, which thus prevents adhesion of water to the gas sensing element 12, so that the gas detection apparatus D continuously can accurately detect an impermissible level of concentration of hydrogen gas in the exhaust gas with adequate sensitivity.

The gas detection apparatus D may be incorporated and used in a fuel cell system installed in a vehicle, or in a variety of systems that has a function of detecting a gas in humid surroundings.

According to the gas detection apparatus D and a gas detection method using the apparatus D as described above, in cases where an anomaly is detected in the gas sensing element 12 as a result of temporary adhesion of water, adhesion of water to the gas sensing element 12 is not facilitated or increased as is the case with a conventional apparatus and method in which heating of a gas detection chamber is suspended upon detection of such an anomaly. Therefore, the gas sensor 1 can be swiftly returned to a normal operable state from an abnormal state (with anomalies) caused by adhesion of water to its gas sensing element.

Moreover, in the gas detection apparatus D, when an anomaly is detected in the gas sensing element 12, the heater 13 continues to heat the gas detection chamber 11a but the output of the heater 13 is lower than usual, so that overheating of the gas detection chamber 11a by the heater 13 can be prevented.

Although the preferred embodiments of the present invention have been described above, various modifications and changes may be made in the present invention without departing from the spirit and scope thereof. For example, the gas sensor 1 in the aforementioned embodiments is attached to the exhaust line 15d provided downstream of the diluter 4; however, the gas sensor 1 may be attached to the air discharge line 15g. Alternatively, the gas sensor 1 may be provided in a system for supplying a fuel gas (hydrogen gas), i.e., hydrogen supply line 15a, hydrogen exhaust line 15c, hydrogen circulation line 15e, purge hydrogen line 15f or any other location where appropriate. In these embodiments of the gas detection apparatus D, the concentration of hydrogen in the gases passing through the system for supplying a fuel gas, such as hydrogen in the gas supplied to the fuel cell stack 2, and hydrogen in the gas purged from the hydrogen exhaust line 15c, can be accurately detected with adequate sensitivity in humid surroundings.

Although the above-described embodiments use a catalytic combustible sensor as the gas sensing element 12, the present invention is not limited to those specific embodiments. Semiconductor gas sensing elements, solid-electrolyte gas sensing elements, electrochemical gas sensing elements, field-effect transistor (FET) gas sensing elements, diode gas sensing elements, adsorption effect transistor (AET) gas sensing elements, and other gas sensing elements or transducers of various types may be employed as the gas sensing element 12.

In the above-described embodiments, the apparatus consistent with the present invention is exemplified by the gas detection apparatus D for detecting the concentration of hydrogen gas in an exhaust gas of the fuel cell stack 2, but the present invention is not limited thereto. The gas detection apparatuses consistent with the present invention may include a variety of apparatuses having a function of detecting a gaseous component (e.g., combustible hydrocarbons, $NO_x$, $SO_x$, hydrogen sulfides, carbon monoxides, carbon dioxides, halogen gases, halogenated hydrogen gases, ammonia gases, etc.) in a gas in humid surroundings.

In the above-described embodiments, the anomaly detection device 8 is comprised of an ammeter (electric current meter) for measuring an electric current carried in the gas sensing element 12; however, the present invention is not limited thereto, and the anomaly detection device 8 applicable to the present invention may include a device (electric resistance meter) for measuring an electric resistance of a coil-shaped platinum wire in the gas sensing element 12, for example.

In the above-described embodiment, the voltage applied to the heater 13 is lowered after detection of anomaly in the gas sensing element 12; however, the present invention is not limited thereto, and it may be possible or preferred in some particular instances that the heater 13 is regulated to continue to heat the gas detection chamber 11a without lowering the voltage of the heater 13.

Furthermore, in another embodiment of the present invention, thus-lowered voltage of the heater 13 may be regulated optionally so that the output of the heater 13 returns to a normal operating level when the anomaly detection device 8 detects absence of the previously detected anomaly of the gas sensor 1 (gas sensing element 12) as a result of removal of water adhered to the gas sensing element 12 by the action of the continuously operated heater 12.

What is claimed is:

1. A gas detection apparatus comprising:
a gas detection chamber adapted to receive a gas that contains moisture;
a gas sensing element provided in the gas detection chamber to detect a component of the gas;
an anomaly detection device provided to detect an anomaly of the gas sensing element;
a heater provided to heat the gas detection chamber to lower a relative humidity in the gas detection chamber; and
a heater regulator provided to regulate an output of the heater, wherein the heater regulator causes the heater to continue to heat the gas detection chamber when the anomaly detection device detects the anomaly of the gas sensing element,
wherein the gas sensing element comprises an element selected from the group consisting of a catalytic combustible sensing element, a semiconductor sensing element, a solid-electrolyte sensing element, an electrochemical sensing element, a field-effect transistor sensing element, a diode sensing element, and an adsorption effect transistor sensing element.

2. A gas detection apparatus comprising:
a gas detection chamber adapted to receive a gas that contains moisture;
a gas sensing element provided in the gas detection chamber to detect a component of the gas;
an anomaly detection device provided to detect an anomaly of the gas sensing element;
a heater provided to heat the gas detection chamber to lower a relative humidity in the gas detection chamber; and
a heater regulator provided to regulate an output of the heater, wherein the heater regulator causes the heater to continue to heat the gas detection chamber when the anomaly detection device detects the anomaly of the gas sensing element,
wherein the anomaly detection device comprises an electric current meter.

3. A gas detection apparatus comprising:
a gas detection chamber adapted to receive a gas that contains moisture;
a gas sensing element provided in the gas detection chamber to detect a component of the gas;
an anomaly detection device provided to detect an anomaly of the gas sensing element;
a heater provided to heat the gas detection chamber to lower a relative humidity in the gas detection chamber; and
a heater regulator provided to regulate an output of the heater, wherein the heater regulator causes the heater to continue to heat the gas detection chamber when the anomaly detection device detects the anomaly of the gas sensing element,
wherein the anomaly detection device comprises an electric resistance meter.

4. A gas detection apparatus comprising:
a gas detection chamber adapted to receive a gas that contains moisture;
a gas sensing element provided in the gas detection chamber to detect a component of the gas;
an anomaly detection device provided to detect an anomaly of the gas sensing element;
a heater provided to heat the gas detection chamber to lower a relative humidity in the gas detection chamber; and
a heater regulator provided to regulate an output of the heater, wherein the heater regulator causes the heater to continue to heat the gas detection chamber when the anomaly detection device detects the anomaly of the gas sensing element,
wherein the component of the gas to be detected by the gas sensing element is a substance selected from the group consisting of combustible hydrocarbon, nitrogen oxide, sulfur oxide, hydrogen sulfide, carbon monoxide, carbon dioxide, halogen, halogenated hydrogen, and ammonia.

5. A fuel cell system comprising:
a fuel cell stack comprised of a plurality of stacked fuel cells each having an anode and a cathode, to generate electricity by electrochemical reaction occurring at a high humidity between a hydrogen fuel gas supplied to the anode and an oxygen gas supplied to the cathode;
a diluter provided downstream of the fuel cell stack to dilute an anode exhaust gas discharged from the anode with a cathode exhaust gas discharged from the cathode; and
a gas detection apparatus comprising:
a gas detection chamber adapted to receive a gas that contains moisture;
a gas sensing element provided in the gas detection chamber to detect a component of the gas;
an anomaly detection device provided to detect an anomaly of the gas sensing element;
a heater provided to heat the gas detection chamber to lower a relative humidity in the gas detection chamber; and
a heater regulator provided to regulate an output of the heater, wherein the heater regulator causes the heater to continue to heat the gas detection chamber when the anomaly detection device detects the anomaly of the gas sensing element;
wherein the component to be detected is hydrogen in the gas passing through the fuel cell system.

6. A fuel cell system according to claim 5, wherein the gas detection chamber of the gas detection apparatus is provided to receive the diluted anode exhaust gas discharged from the diluter.

7. A fuel cell system according to claim 5, wherein the gas detection chamber of the gas detection apparatus is provided to receive the anode exhaust gas discharged from the anode and to be introduced into the diluter.

8. A fuel cell system according to claim 5, wherein the gas detection chamber of the gas detection apparatus is provided to receive the hydrogen fuel gas to be supplied to the anode.

9. A fuel cell system according to claim 5, wherein the gas detection chamber of the gas detection apparatus is provided to receive the anode exhaust gas discharged from the anode.

10. A fuel cell system according to claim 9, wherein the gas detection chamber of the gas detection apparatus is provided to receive the anode exhaust gas that flows through a hydrogen exhaust line (15c).

11. A fuel cell system according to claim 9, wherein the gas detection chamber of the gas detection apparatus is provided to receive the anode exhaust gas that flows through a hydrogen circulation line (15e).

12. A fuel cell system according to claim 9, wherein the gas detection chamber of the gas detection apparatus is provided to receive the anode exhaust gas that flows through a purge hydrogen line (15f).

* * * * *